United States Patent [19]

Phaff

[11] Patent Number: 4,920,220
[45] Date of Patent: Apr. 24, 1990

[54] CHROMOGENIC 1-HETEROCYCLIC SUBSTITUTED 2,4-BENZOXAZINES

[75] Inventor: Rox Phaff, Rheinfelden, Switzerland

[73] Assignee: Ciba-Geigy Corporation, Ardsley, N.Y.

[21] Appl. No.: 265,645

[22] Filed: Nov. 1, 1988

[30] Foreign Application Priority Data

Nov. 12, 1987 [CH] Switzerland ................. 4418/87

[51] Int. Cl.$^5$ ........................... C07D 413/04
[52] U.S. Cl. ................................... 544/90
[58] Field of Search ......................... 544/90

[56] References Cited

U.S. PATENT DOCUMENTS

| 4,070,508 | 1/1978 | Ishige et al. ............. 427/282 |
| 4,831,141 | 5/1989 | Berneth et al. ............ 544/90 |
| 4,835,270 | 5/1989 | Berneth .................. 544/73 |

FOREIGN PATENT DOCUMENTS 0187329 7/1986 European Pat. Off. .

OTHER PUBLICATIONS

R. M. Acheson, An Introduction to the Chemistry of Heterocyclic Compounds, Interscience Publishers, New York (1960) pp. 127–132, 150–152 and 154–157.

Primary Examiner—Richard L. Raymond
Attorney, Agent, or Firm—George R. Dohmann; Edward McC. Roberts

[57] ABSTRACT

Chromogenic 1-heterocyclic substituted 2,4-benzoxazines of formula

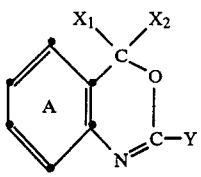

wherein $X_1$ and $X_2$ are identical or different monocyclic or polycyclic heteroaromatic radicals and $X_2$ is also an aryl radical, Y is hydrogen, alkyl, cycloalkyl, aryl, aralkyl or a heterocyclic radical, and the benzene ring A is substituted by halogen, cyano, nitro, lower alkyl, lower alkoxy, lower alkylthio, lower alkylcarbonyl, lower alkoxycarbonyl or $-NR_1R_2$, in which $R_1$ and $R_2$ are each independently of the other hydrogen, alkyl of not more than 12 carbon atoms which is unsubstituted or substituted by halogen, hydroxy, cyano or lower alkoxy, or are cycloalkyl of 5 to 10 carbon atoms, or phenalkyl or phenyl, each unsubstituted or ring-substituted by halogen, cyano, lower alkyl or lower alkoxy, or $-NR_1R_2$ is a 5- or 6-membered, preferably saturated, heterocyclic radical.

These benzoxazines are particularly suitable for use as color formers in pressure-sensitive or heat-sensitive recording materials and give strong and lightfast orange, pink, red, violet, green, greenish-blue, violet blue, grey or black colorations.

12 Claims, No Drawings

CHROMOGENIC 1-HETEROCYCLIC SUBSTITUTED 2,4-BENZOXAZINES

The present invention relates to chromogenic 1-heterocyclic substituted 2,4-benzoxazines, to their preparation, and to the use thereof as colour formers in pressure-sensitive or heat-sensitive recording materials.

The chromogenic compounds of this invention have the general formula

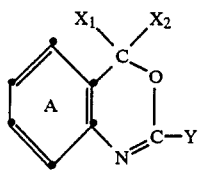

(1)

wherein $X_1$ and $X_2$ are identical or different monocyclic or polycyclic heteroaromatic radicals and $X_2$ is also an aryl radical, Y is hydrogen, alkyl, cycloalkyl, aryl, aralkyl or a heterocyclic radical, and the benzene ring A is substituted by halogen, cyano, nitro, lower alkyl, lower alkoxy, lower alkylthio, lower alkylcarbonyl, lower alkoxycarbonyl or $-NR_1R_2$, in which $R_1$ and $R_2$ are each independently of the other hydrogen, alkyl of not more than 12 carbon atoms which is unsubstituted or substituted by halogen, hydroxy, cyano or lower alkoxy, or $R_1$ and $R_2$ are cycloalkyl of 5 to 10 carbon atoms, or phenalkyl or phenyl, each unsubstituted or ring-substituted by halogen, cyano, lower alkyl or lower alkoxy, or $-NR_1R_2$ is a 5- or 6-membered, preferably saturated, heterocyclic radical.

Within the scope of the definition of the benzoxazines, lower alkyl, lower alkoxy and lower alkylthio denote those groups or moieties which contain 1 to 5, preferably 1 to 3, carbon atoms. Examples of such groups are: methyl, ethyl, n-propyl, isopropyl, n-butyl, sec-butyl, amyl or isoamyl; methoxy, ethoxy, isopropoxy, isobutoxy or tert-butoxy; and methylthio, ethylthio, propylthio or butylthio.

Halogen is, for example, fluorine, bromine or, preferably, chlorine.

The heteroaromatic radicals $X_1$ and $X_2$ are preferably attached to the oxazine ring through a carbon atom of the heterocyclic ring.

Such heteroaromatic radicals $X_1$ and $X_2$ are, for example, pyrrolyl, thienyl, indolyl, benzofuranyl, benzothienyl or naphthothienyl.

The monocyclic or polycyclic heteroaromatic radicals can carry one or more substituents in the ring. Suitable C-substituents are halogen, hydroxyl, cyano, nitro, lower alkyl, lower alkoxy, lower alkoxycarbonyl, acyl of 1 to 8 carbon atoms, preferably lower alkylcarbonyl, amino, lower alkylamino or di-lower alkylamino, $C_5$-$C_6$cycloalkyl, benzyl or phenyl, whereas N-substituents are typically $C_1$-$C_{12}$alkyl, $C_2$-$C_{12}$alkenyl, $C_1$-$C_8$acyl, benzyl or phenethyl, each of which may be substituted, for example, by cyano, halogen, nitro, hydroxy, lower alkyl, lower alkoxy or lower alkoxycarbonyl.

The alkyl and alkenyl radicals may be straight chain or branched and are, for example, methyl, ethyl, n-propyl, isopropyl, n-butyl, tert-butyl, sec-butyl, amyl, n-hexyl, 2-ethyl-n-hexyl, isooctyl, n-octyl, decyl or dodecyl, and, respectively, vinyl, allyl, 2-methylallyl, 2-ethylallyl, 2-butenyl or octenyl.

Acyl is preferably formyl, lower alkylcarbonyl, for example acetyl or propionyl, or benzoyl. Further acyl radicals may be lower alkylsulfonyl such as methylsulfonyl or ethylsulfonyl as well as phenylsulfonyl. Benzoyl and phenylsulfonyl can be substituted by halogen, methyl, methoxy or ethoxy.

Preferred heteroaromatic radicals are substituted 2-pyrrolyl or, in particular, 3-indolyl radicals, for example $N-C_1-C_8$alkylpyrrol-2-yl or $N-C_1-C_8$alkyl-2-methylindol-3-yl radicals. Preferably $X_1$ denotes such radicals.

$X_2$ as aryl can be a phenyl or naphthyl radical, each unsubstituted or substituted by halogen, cyano, lower alkyl, cycloalkyl, acyl, acylamino, $-NR_3R_4$, $-OR_3$ or $-SR_3$.

Preferably $X_2$ is a substituted phenyl radical of formula

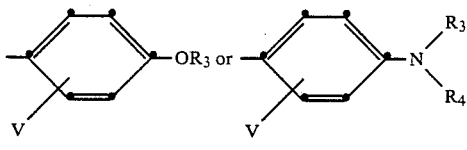

(1a)        (1b)

$R_3$ and $R_4$, each independently of the other, have the same meaning as given for $R_1$ and $R_2$.

In formulae (1a) and (1b) V is hydrogen, halogen, lower alkyl, $C_1$-$C_{12}$-alkoxy, $C_1$-$C_{12}$acyloxy, benzyl, phenyl, benzyloxy, phenoxy, or benzyl or benzyloxy, each substituted by halogen, cyano, lower alkyl or lower alkoxy, or is the group $-NT_1T_2$, wherein $T_1$ and $T_2$, each independently of the other, are hydrogen, lower alkyl, cycloalkyl, benzyl or benzyl which is substituted by halogen, cyano, lower alkyl or lower alkoxy, or are $C_1$-$C_8$acyl, and $T_1$ is also phenyl or phenyl which is substituted by halogen, cyano, lower alkyl or lower alkoxy. V is preferably located ortho to the carbon bond.

$R_1$, $R_2$, $R_3$, $R_4$ and Y as alkyl groups can be straight chain or branched alkyl radicals. Examples of such radicals are: methyl, ethyl, n-propyl, isopropyl, n-butyl, sec-butyl, tert-butyl, amyl, isoamyl, n-hexyl, 2-ethyl-n-hexyl, n-heptyl, n-octyl, isooctyl, n-nonyl, isononyl or n-dodecyl.

$R_1$, $R_2$, $R_3$ and $R_4$ as substituted alkyl radicals are preferably cyanoalkyl, haloalkyl, hydroxyalkyl, alkoxyalkyl, each preferably having a total of 2 to 6 carbon atoms. Examples of such radicals are: β-cyanoethyl, β-chloroethyl, β-hydroxyethyl, β-methoxyethyl and β-ethoxyethyl.

$R_1$, $R_2$, $R_3$, $R_4$, Y, $T_1$ and $T_2$ as cycloalkyl can be cyclopentyl, cycloheptyl or, preferably, cyclohexyl. The cycloalkyl radicals can contain one or more $C_1$-$C_4$alkyl radicals, preferably methyl groups, and contain a total of 5 to 10 carbon atoms.

An acyloxy radical V is, for example, formyloxy, lower alkanoyloxy or benzoyloxy. V as $C_1$-$C_{12}$alkoxy can be a straight chain or branched group, for example methoxy, ethoxy, isopropoxy, tert-butoxy, n-hexyloxy, octyloxy or dodecyloxy.

If $-NR_1R_2$ and $-NR_3R_4$ are each a heterocyclic radical, then said radical is, for example, pyrrolidino, piperidino, pipecolino, morpholino, thiomorpholino or piperazino such as N-methylpiperazino. Preferred saturated heterocyclic radicals —NR$_1$R$_2$ and —NR$_3$R$_4$ are pyrrolidino, piperidino or morpholino.

The substituents R$_1$, R$_2$, R$_3$ and R$_4$ are preferably cyclohexyl, benzyl, phenethyl, cyano-lower alkyl, for example β-cyanoethyl or, most preferably, lower alkyl such as methyl or ethyl. —NR$_1$R$_2$ and —NR$_3$R$_4$ are also preferably pyrrolidinyl.

V may with advantage be hydrogen, halogen, lower alkyl, e.g. methyl, or benzyloxy, C$_1$-C$_8$alkoxy, preferably lower alkoxy such as methoxy, ethoxy, isopropoxy or tert-butoxy, or the —NT$_1$T$_2$ group, where one of T$_1$ and T$_2$ is preferably C$_1$-C$_8$acyl or lower alkyl and the other is hydrogen or lower alkyl. The acyl radical is in this case preferably lower alkylcarbonyl, e.g. acetyl or propionyl. Preferably V is acetylamino, dimethylamino, benzyloxy or, most preferably, lower alkoxy and, in particular, ethoxy or hydrogen.

A heterocyclic radical Y is most preferably a 5- or 6-membered heterocycle having aromaticity and containing preferably oxygen, sulfur or nitrogen. Examples of such heterocycles are: thienyl, furyl, pyrrolyl, pyrazolyl, imidazolyl or pyridyl radicals.

Y is preferably phenyl or phenyl which is substituted by halogen, trifluoromethyl, cyano, lower alkyl or lower alkoxy.

The benzene ring A may contain 1 to 3 substitutents. The substituents are preferably located meta and/or para to the nitrogen bond.

The ring A is preferably a benzene ring which contains a lower alkoxy radical or the group —NR$_1$R$_2$ in meta-position to the nitrogen bond. This benzene ring A is preferably further substituted by halogen, lower alkoxy or lower alkyl, preferably in para-position to the nitrogen bond.

Useful heterocyclic substituted 2,4-benzoxazines are those of formula

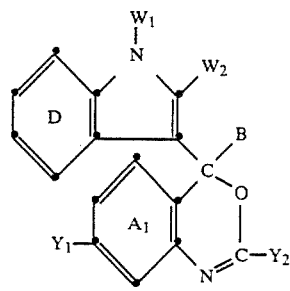

(2)

wherein B is a substituted phenyl radical of formula

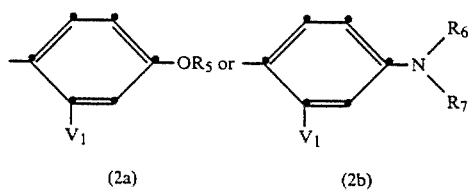

Y$_1$ is lower alkoxy or di-lower alkylamino, Y$_2$ is phenyl or phenyl which is substituted by halogen, trifluoromethyl, lower alkyl or lower alkoxy, W$_1$ is hydrogen, C$_1$-C$_8$alkyl or C$_1$-C$_8$alkyl which is substituted by cyano or lower alkoxy, or is acetyl, propionyl or benzyl, W$_2$ is lower alkyl, preferably methyl, or phenyl, R$_5$, R$_6$ and R$_7$ are each independently alkyl of not more than 12 carbon atoms which is unsubstituted or substituted by hydroxy, cyano or lower alkoxy, or are C$_5$-C$_6$cycloalkyl, benzyl, phenethyl or phenyl, or —NR$_6$R$_7$ is pyrrolidino, piperidino or morpholino, V$_1$ is hydrogen, halogen, lower alkyl, C$_1$-C$_8$alkoxy, benzyloxy or the group —NT$_3$T$_4$, T$_3$ and T$_4$ are each independently of the other hydrogen, lower alkyl, lower alkylcarbonyl or benzoyl or benzoyl which is substituted by halogen, methyl or methoxy, and the rings A$_1$ and D$_1$ are each independently of the other unsubstituted or substituted by halogen or, preferably, lower alkyl such as methyl.

Among the compounds of formula (2), the benzoxazines in which B is a substituted phenyl radical of formula (2a), V$_1$ is hydrogen, W$_1$ is C$_1$-C$_8$alkyl, W$_2$ is methyl and Y$_1$ is lower alkoxy, are preferred.

Particularly interesting benzoxazines are those of formula

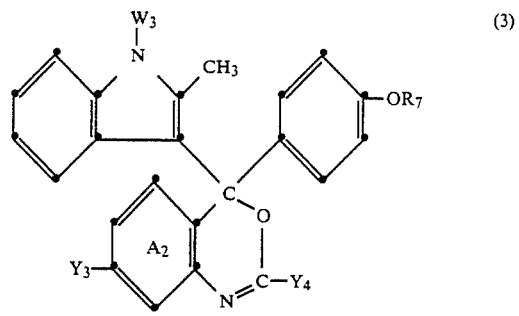

(3)

wherein A$_2$ is unsubstituted or preferably substituted by halogen or methyl in para-position to the nitrogen bond, Y$_3$ is lower alkoxy, preferably methoxy, R$_7$ and W$_3$ are each independently of the other lower alkyl, and Y$_4$ is phenyl, tolyl or chlorophenyl.

The benzoxazines of formulae (1) to (3) are prepared by oxidising and cyclising a methine compound of formula

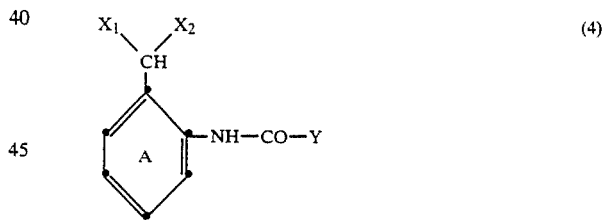

(4)

wherein A, X$_1$, X$_2$ and Y are as defined above.

The oxidation of the leuco compound of formula (4) to the benzoxazine of formula (1) is effected with an oxidising agent. Oxidising agents which may be suitably employed are chromates, bichromates, chlorates, chlorites, nitrites, perborates, permanganates, peroxides, for example hydrogen peroxide, manganese dioxide, lead dioxide, molecular oxygen, air, chloroanil, salts of hexacyanoferrate(III) such as potassium or sodium salts or iron(III) chloride hexahydrate.

The oxidation is carried out at room temperature or slightly elevated temperature (30° to 50° C.), preferably in an organic solvent which may be used with an acid.

Suitable solvents that form the reaction medium are alcohols such as ethanol, propanol, ethylene glycol monomethyl or monoethyl ether, ketones, such as acetone, butanone or methyl isopropyl ketone, dimethyl sulfoxide, or nitriles of aliphatic monocarboxylic acids, for example acetonitrile, propionitrile or butyronitrile, cycloaliphatic or aromatic hydrocarbons such as cyclohexane, benzene, toluene or xylene; chlorinated hydrocarbons such as ethylene chloride, tetrachloroethylene or chlorobenzenes, for example chlorobenzene, chlorotoluene or dichlorobenzene; or cyclic ethers such as dioxane or tetrahydrofuran.

Acids which may be used concomitantly are, for example, hydrochloric acid, phosphoric acid, acetic acid or propionic acid. Mixtures of the cited solvents and acids may also be used.

The cyclisation and isolation of the final product of formula (1) is carried out in generally known manner by adjusting the pH of the oxidation mixture to at least 6, preferably to a value from 7 to 11, for example with an alkali such as an alkali metal hydroxide, ammonia, an alkali metal carbonate or bicarbonate, and isolating, washing and drying the precipitate, or by treatment with a suitable organic solvent such as methanol, isopropanol, benzene, chlorobenzene, toluene or, preferably, propanol.

The leuco compounds of formula (4) used as starting materials can be prepared by reacting a carbinol compound of formula

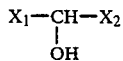  (5)

with an amino compound of formula

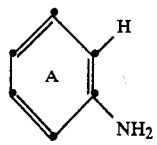  (6)

and acylating the resultant methine compound of formula

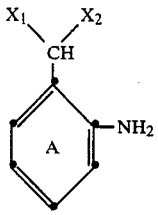  (7)

with a compound that introduces the radical Y—CO— in conventional manner, in which formulae above A, $X_1$, $X_2$ and Y have the given meanings. The substituents of the benzene ring A are preferably in meta- and/or para-position to the amino group.

The reaction of the carbinol compound of formula (5) with the amino compound of formula (6) is conveniently carried out in a polar organic solvent, preferably in a lower aliphatic alcohol, for example methanol, ethanol or isopropanol, or in an ether such as tetrahydrofuran, and preferably in the presence of an acid catalyst. The condensation can be carried out at room temperature (20°–25° C.). It is, however, expedient to perform the reaction at elevated temperature up to reflux temperature, preferably in the range from 40° to 100° C. Suitable acid catalysts are inorganic acids such as hydrochloric acid, sulfuric acid, phosphoric acid or perchloric acid, as well as lower aliphatic carboxylic acids such as formic acid or acetic acid.

Suitable acylating agents for introducing the acyl radical Y—CO— are reactive functional derivatives of aliphatic or cycloaliphatic carboxylic acids, preferably carbonyl halides or carboxylic anhydrides, for example acetyl bromide, acetyl chloride or acetic anhydride or, more particularly, of aromatic carboxylic acids such as unsubstituted or ring-substituted benzyl halides.

A further process for the preparation of the leuco compounds of formula (4) comprises reacting an amide of formula

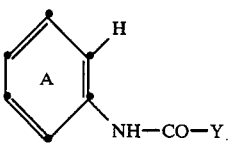  (8)

with a ketone of formula

  (9)

wherein A, $X_1$, $X_2$ and Y are as defined above.

The reaction is normally carried out with condensing agents in the absence or in the presence of inert organic solvents in the temperature range from room temperature to the boiling point of the respective medium.

The benzoxazines of formulae (1) to (3) are normally colourless or, at most, faintly coloured. When these colour formers are brought into contact with preferably an acid developer, i.e. an electron acceptor, they produce, depending on the meaning of A, $X_1$ and $X_2$ and on the developer, strong orange, pink, red, violet, green, greenish-blue, blue, violet-blue, grey or black shades which are fast to sublimation and, in particular, light.

The benzoxazines of formulae (1) to (3) are therefore also very useful when combined with one or more other known colour formers, for example 3,3-(bisaminophenyl)phthalides, 3-indolyl-3-aminophenylazaphthalides, 3,3-(bisindolyl)phthalides, 3-aminofluoranes, 2,6-diaminofluoranes, 2,6-diamino-3-methylfluoranes, leucoauramines, spiropyranes, spirodipyranes, chromenoindoles, chromenopyrazoles, phenoxazines, phenothiazines, quinazolines, rhodamine lactams, carbazolylmethanes or other triarylmethaneleuco dyes, to give blue, navy blue, grey or black colorations.

The benzoxazines of formulae (1) to (3) exhibit on activated clays as well as on phenolic substrates an excellent colour intensity and especially lightfastness. They are suitable in particular as rapidly developing colour formers for use in a heat-sensitive, or especially in a pressure-sensitive, recording material which can also be a copying material. They are distinguished by the property that they are pH-stable and that they are highly soluble in the capusule oils. After exposure on a CB sheet, they exhibit a slight decrease in colour strength (CB decline).

A pressure-sensitive material comprises, for example, at least one pair of sheets which contain at least one colour former of formulae (1) to (3), dissolved in an organic solvent, and an electron acceptor as developer.

Typical examples of such developers are activated clays such as attapulgite, acid clay, bentonite, montmorillonite, activated clay, e.g. acid-activated bentonite or montmorillonite, and also zeolith, halloysite, silica, alumina, aluminium sulfate, aluminium phosphate, zinc chloride, zinc nitrate, activated kaolin or any clay. Suitable developers are also acidic organic compounds, for example unsubstituted or ring-substituted phenols, resorcinols, salicylic acids, e.g. 3,5-bis($\alpha,\alpha$-dimethylbenzyl)-salicylic acid or 3,5-bis($\alpha$-methylbenzyl)salicylic acid, or salicylates and their metal salts, e.g. zinc salts, or an acidic polymer, for example a phenolic polymer, an alkylphenol acetylene resin, a maleic acid/rosin resin or a partially or completely hydrolysed polymer of maleic acid and styrene, ethylene or vinyl methyl ether, or carboxymethylene. Mixtures of these monomers and polymers can also be used. Particularly preferred developers are acid-activated bentonite, zinc salicylates or the condensates of p-substituted phenols with formaldehyde. These latter may also be modified with zinc.

The developers may also be used in admixture with other basically inert or almost inert pigments or with other auxiliaries such as silica gel or UV absorbers, e.g. 2-(2-hydroxyphenyl)benzotriazoles. Examples of such pigments are: talcum, titanium dioxide, alumina, aluminium hydroxide, zinc oxide, chalk, clays such as kaolin, as well as organic pigments, e.g. urea/formaldehyde condensates (BET surface area: 2–75 m$^2$/g) or melamine/formaldehyde condensates.

The colour former effects a coloured marking at those points where it comes into contact with the electron acceptor. To prevent the colour formers contained in the pressure-sensitive recording material from becoming active prematurely, they are usually separated from the electron acceptor. This separation can conveniently be accomplished by incorporating the colour formers in foam-like, sponge-like or honeycomb-like structures. The colour formers are preferably encapsulated in microcapsules, which can normally be ruptured by pressure.

When the capsules are ruptured by pressure, for example with a pencil, the colour former solution is transferred to an adjacent sheet which is coated with an electron acceptor and a coloured area is thereby produced. This colour results from the dye which is formed and which is absorbed in the visible range of the electromagnetic spectrum.

The colour formers are encapsulated preferably in the form of solutions in organic solvents. Examples of suitable solvents are preferably non-volatile solvents, for example a polyhalogenated paraffin, such as chloroparaffin, or a polyhalogenated diphenyl, such as monochlorodiphenyl or trichlorodiphenyl, and also tricresyl phosphate, di-n-butyl phthalate, dioctyl phthalate, trichlorobenzene, trichloroethyl phosphate, an aromatic ether such as benzylphenyl ether, a hydrocarbon oil such as paraffin or kerosene, an alkylated, e.g. an isopropyl, isobutyl, sec- or tert-butyl derivative of diphenyl, diphenylalkane, napthalene or terphenyl; dibenzyl toluene, terphenyl, partially hydrogenated terphenyl, a benzylated xylene, or other chlorinated or hydrogenated, condensed aromatic hydrocarbons. Mixtures of different solvents, especially mixtures of paraffin oils or kerosene and diisopropylnaphthalene or partially hydrogenated terphenyl, are often used in order to obtain an optimum solubility for the colour formation, a rapid and strong coloration, and a viscosity which is advantageous for the microencapsulation. When encapsulated, the benzoxazines of this invention are distinguished by exceedingly good pH stability, e.g. in the pH range from 4 to 10.

The capsules walls can be formed evenly around the droplets of the colour former solution by coacervation; and the encapsulating material is as described e.g. in U.S. Pat. No. 2,800,457. The capsules can also be formed preferably from an aminoplast or a modified aminoplast by polycondensation, as described in British patent specification Nos. 989,264, 1,156,725, 1,301,052 and 1,355,124. Also suitable are microcapsules which are formed by interfacial polymerisation, e.g. capsules formed from polyester, polycarbonate, polysulfonamide, polysulfonate, but in particular from polyamide or polyurethane.

The microcapsules containing the colour formers of formulae (1) to (3) can be used for the production of a wide range of known kinds of pressure-sensitive copying materials. The various systems differ substantially from one another in the arrangement of the capsules and of the colour reactants, and in the support. A preferred arrangement is that in which the encapsulated colour former is in the form of a layer on the back of a transfer sheet and the developer is in the form of a layer on the face of a receiver sheet.

Another arrangement of the components is that wherein the microcapsules containing the colour former and the developer are in or on the same sheet, in the form of one or more individual layers, or are present in the paper pulp.

The capsules are preferably secured to the support by means of a suitable adhesive. As paper is the preferred support, these adhesives are principally paper-coating agents, for example gum arabic, polyvinyl alcohol, hydroxymethylcellulose, casein, methyl cellulose, dextrin, starch or starch derivatives or polymer latices. These latter are e.g. butadiene/styrene copolymers or acrylic homopolymers or copolymers.

The paper employed comprises not only normal paper made from cellulose fibres, but also paper in which the cellulose fibres are replaced (partially or completely) by synthetic polymers.

The compounds of formulae (1) to (3) can also be employed as colour formers in a thermoreactive recording material. This recording material usually contains at least one carrier, one colour former, one electron acceptor and, in some cases, also a binder and/or wax.

Thermoreactive recording systems comprise, for example, heat-sensitive recording or copying materials or papers. These systems are used e.g. for recording information, for example in electronic computers, teleprinters or telewriters, or in recording and measuring instruments, e.g. electrocardiographs. The image (mark) formation can also be effected manually with a heated pen. Laser beams can also be used to produce heat-induced marks.

The thermoreactive recording material can be composed such that the colour former is dispersed or dissolved in one binder layer and the developer is dissolved or dispersed in the binder in a second layer. An alternative method comprises dispersing both the colour former and the developer in one layer. By means of heat the binder is softened at specific areas and the colour former comes into contact with the electron acceptor at those points where heat is applied and the desired colour develops at once.

Suitable developers are the same electron acceptors as are used in pressure-sensitive papers. Examples of developers are the already mentioned clays and phenolic resins, or also the phenolic compounds described e.g. in German Offenlegungsschrift 1,251,348, for example 4-tert-butylphenol, 4-phenylphenol, methylene-bis(p-phenylphenol), 4-hydroxydiphenyl ether, $\alpha$-naphthol, β-naphthol, methyl 4-hydroxybenzoate or benzyl 4-hydroxybenzoate, 4-hydroxydiphenylsulfone, 4'-hydroxy-4-methyldiphenylsulfone, 4'-hydroxy-4-isopropoxydiphenylsulfone, 4-hydroxyacetophenone, 2,2'-dihydroxydiphenyl, 4,4'cyclohexylidenediphenol, 4,4'-isopropylidenediphenol, 4,4'-isopropylidenebis(2-methylphenol), an antipyrine complex of zinc thiocyanate, a pyridine complex of zinc thiocyanate, 4,4'-bis(hydroxyphenyl)valeric acid, hydroquinone, pyrogallol, phloroglucinol, p-, m- and o-hydroxybenzoic acid, gallic acid, 1-hydroxy-2-naphthoic acid, as well as boric acid or organic, preferably aliphatic, dicarboxylic acids, for example tartaric acid, oxalic acid, maleic acid, citric acid, citraconic acid or succinic acid.

Fusible, film-forming binders are preferably used for the manufacture of the thermoreactive recording material. These binders are normally water-soluble, whereas the benzoxazines and the developer are sparingly soluble or insoluble in water. The binder should be able to disperse and fix the colour former and the developer at room temperature.

When heat is applied, the binder softens or melts, so that the colour former comes in contact with the developer and a colour is able to form. Examples of binders which are soluble, or at least swellable, in water are e.g. hydrophilic polymers such as polyvinyl alcohol, polyacrylic acid, hydroxyethylcellulose, methyl cellulose, carboxmethylcellulose, polyacrylamide, polyvinyl pyrrolidone, carboxylated butadiene/styrene copolymers, gelatin, starch, or etherified corn starch.

If the colour former and the developer are in two separate layers, it is possible to use water-insoluble binders, i.e. binders which are soluble in non-polar or only weakly polar solvents, for example natural rubber, synthetic rubber, chlorinated rubber, alkyd resins, polystyrene, styrene/butadiene copolymers, polymethylacrylates, ethyl cellulose, nitrocellulose or polyvinyl carbazole. The preferred arrangement, however, is that in which the colour former and the developer are contained in one layer in a water-soluble binder.

The thermoreactive coatings may contain further ingredients. To improve the degree of whiteness, to facilitate the printing of papers, and to prevent the heated pen from sticking, the coatings may contain e.g. talcum, titanium dioxide, zinc oxide, aluminium hydroxide, calcium carbonate (e.g. chalk), clays or also organic pigments, for example urea/formaldehyde polymers. In order to effect the colour formation only within a limited temperature range, it is possible to add substances such as urea, thiourea, diphenyl thiourea, acetamide, acetanilide, benzosulfanilide, stearamide, phthalic anhydride, metal stearates such as zinc stereate, dimethyl terephthalate, phthalonitrile or other appropriate fusible products which induce the simultaneous melting of the colour former and the developer. Thermographic recording materials preferably contain waxes, e.g. carnauba wax, montana wax, paraffin wax, polyethylene wax, condensates of higher fatty acid amides and formaldehyde, or condensates of higher fatty acids and ethylenediamine.

A further utility of the compounds of formulae (1) to (3) is the production of a coloured image with the photocurable microcapsules described in German Offenlegungsschrift 3,247,488.

The invention is illustrated by the following Examples, in which percentages are by weight, unless otherwise indicated.

EXAMPLE 1

179.22 g of dimethyl anisamide are added at 20°–25° C. to 91.73 g of phosphoroxy chloride and then 67.5 g of 2-methylindole are added, whereupon the temperature rises to 45° C. As soon as the temperature begins to fall, the mixture is heated to 100° C. over 1 hour, then cooled to 30° C. and 178 g of sodium hydroxide in 500 ml water are added dropwise. A further 500 ml of water are then added and the mixture is stirred for 10 hours at room temperature and then filtered. The granular product so obtained is comminuted and boiled for 90 minutes in 600 ml of ethanol. After cooling to 10° C., the product is isolated by filtration and washed with ethanol and dried, affording 87.9 g of a pink ketone of formula

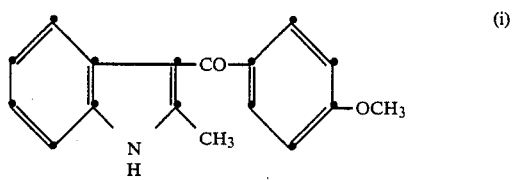

which melts at 212°–213° C.

87.7 g of the above compound are dissolved at 40°–50° C. in 500 ml of dimethyl sulfoxide and the solution is cooled to room temperature. Then 124 ml of a 10N aqueous solution of potassium hydroxide are added and 37 ml of ethyl bromide are added dropwise over 30–45 minutes. The reaction mixture is stirred for 2 hours, poured into 4 liters of water, and extracted with methylene chloride. The extract is treated with activated carbon, dried over sodium sulfate and concentrated, affording 92.6 g of an oil which crystallises gradually. Recrystallisation from 2-propanol gives 84.3 g of a compound of formula

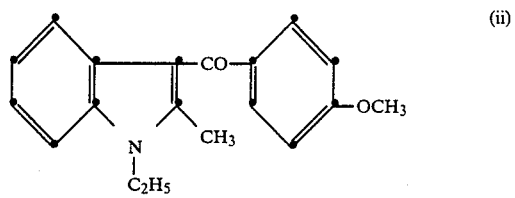

which melts at 104°–105° C.

84.3 g of the compound of formula (ii) are dissolved in tetrahydrofuran and the solution is added dropwise to 5.44 g of lithium aluminium hydride in 250 ml of tetrahydrofuran. After 1 hour a further 2.7 g of lithium aluminium hydride are added. After 30 minutes at room temperature, 15.3 ml of ethyl acetate and 8 ml of water are added dropwise at 5°–10° C. The mixture is treated with sodium sulfate and activated carbon, then filtered and the filtrate is concentrated, to give 84.4 g of a compound of formula

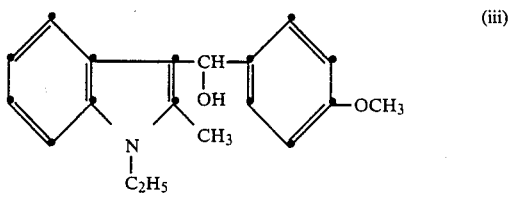

in the form of an oil.

84.4 g of the compound of formula (iii) are dissolved in 290 ml of methanol and to the solution are added 39.3 g of 4-amino-2-methoxytoluene. Then 1.5 ml of concentrated hydrochloric acid are added and the mixture is refluxed for 1 hour. The resultant suspension is cooled to 0° C. and filtered. The filter residue is washed with methanol, affording 108.7 g of a compound of formula

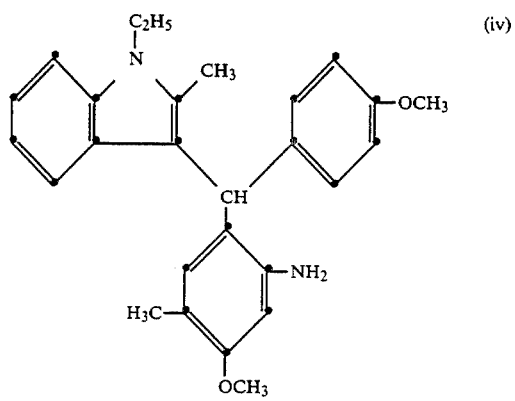

(iv)

which melts at 171°–172° C.

17.3 g of the compound of formula (iv) are suspended in 42 ml of dichloroethane and 5.9 g of benzoyl chloride in 18 ml of dichloroethane are added to the suspension over 20–30 minutes. The resultant solution is stirred for 1 hour at 30°–40° C. and then concentrated. The residue is taken up in 63 ml of ethanol and 25 ml of a 10% solution of sodium hydroxide are added. The precipitate is isolated by filtration and dried. Recrystallisation from toluene gives 14.3 g of a compound of formula

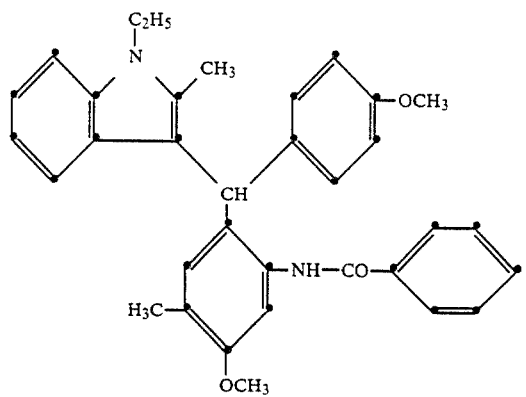

(v)

which melts at 207°–208° C.

2.5 g of the compound of formula (v) are dissoslved in 25 ml of acetone and 11.7 g of iron(III) chloride hexahydrate are added to the solution. The acetone is removed after 5 hours, the residue is taken up in 50 ml of toluene and the solution is washed with 80 ml of a 10% solution of sodium hydroxide. The organic phase is separated, treated with activated carbon, dried over sodium sulfate and concentrated. The residue is recrystallised from 2-propanol/water, to give 1.57 g of a compound of formula

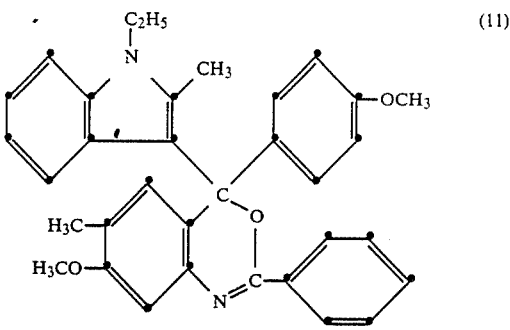

(11)

which melts at 137°–147° C.

This compound produces a pink image of very good lightfastness on acid clay.

EXAMPLE 2

10.4 g of the compound of formula (iv) according to Example 1 are added to 25 ml of dichloroethane and to this solution is added a solution of 4.4 g of 4-chlorobenzoyl chloride in 10 ml of dichloroethane at 20°–30° C. over 45 minutes. The reaction mixture is stirred for 1 hour at 30°–40° C. and then the solvent is removed. The residue is stirred in 37 ml of diethyl ether and 15 ml of a 10% solution of sodium hydroxide. After dilution with water and extraction with methylene chloride, the organic phase is washed with water, treated with activated carbon, dried over sodium sulfate and concentrated. The residue is dissolved in diethyl ether and precipitated with petroleum ether. The precipitate is isolated by filtration and washed with petroleum ether, to give 9.0 g of a leuco compound of formula

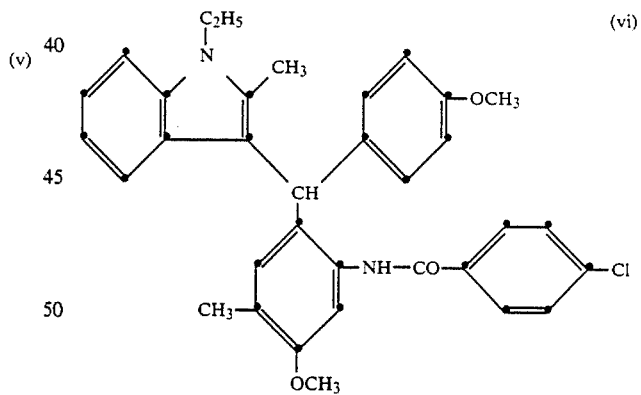

(vi)

which melts at 164°–165° C.

2.5 g of the compound of formula (vi) are dissolved in 25 ml of acetic acid and to the solution are added 6 g of iron(III) chloride hexahydrate. The solution is stirred for 90 minutes at room temperature and then poured into 400 ml of water. While cooling with ice, the batch is made alkaline with 100 ml of concentrated sodium hydroxide solution and extracted with toluene. The organic phase is treated with activated carbon, dried over sodium sulfate and concentrated. The residue is chromatographed over silica gel with a 2:1 mixture of hexane/ether as eluant, affording 0.6 g of a benzoxazine of formula

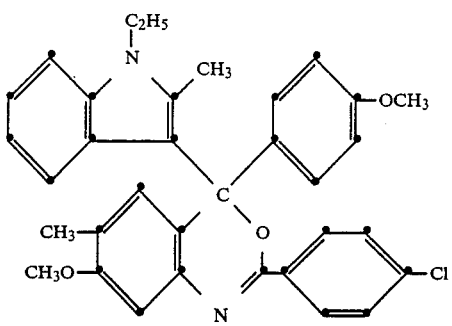

which melts at 120°–122° C.

This compound gives a pink coloration on acid clay.

EXAMPLE 3

6.5 g of a compound of formula

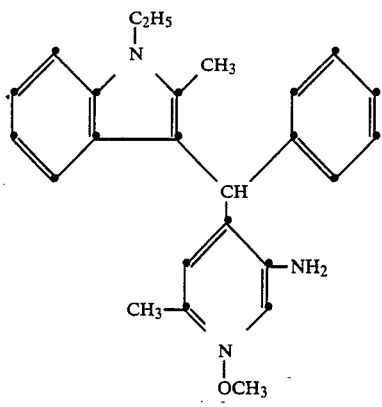

are suspended in 17 ml of dichloroethane. A solution of 2.6 g of benzoyl chloride in 7 ml of dichloroethane is then added dropwise at 20°–30° C. over 45 minutes. The mixture is stirred for 30 minutes at 30°–35° C., then the solvent is removed under vacuum, the residue is dissolved in 25 ml of ethanol, and 10 ml of a 10% solution of sodium hydroxide are added to the solution. The gradually precipitated product is isolated by filtration, washed with a 3:1 mixture of water/ethanol and dried, affording 5.1 g of a compound of formula

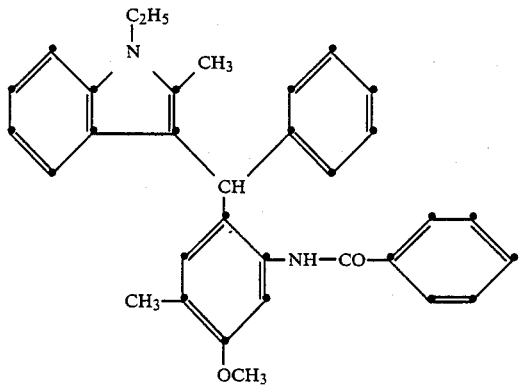

which melts at 170°–171° C.

2.44 g of the compound of formula (viii) are dissolved in 25 ml of acetone and the solution is stirred with 10.8 g of iron(III) chloride hexahydrate for 14 hours at romm temperature. The solvent is removed and the residue is taken up in water and the solution is made alkaline with 20 ml of concentrated sodium hydroxide solution. The mixture is extracted with toluene and the extract is treated with activated carbon, filtered, and the organic phase is separated. The toluene is removed and the residue is recrystallised from 2-propanol/water, to give 1.7 g of the benzoxazine of formula

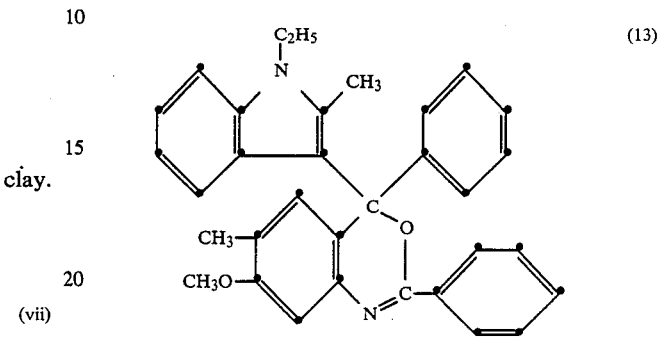

which melts at 168°–169° C.

This compound produces a pink image of good light-fastness on acid clay.

EXAMPLE 4

16.5 g of (1-ethyl-2-methylindol-3-yl)-(4-anisyl)carbinol are dissolved in 60 ml of methanol and 13.5 g of 3-dimethylaminobenzanilide are added to the solution. The mixture is heated to 65° C., diluted with 50 ml of methanol after 15 minutes, and stirred for 12 hours at 65° C. The batch is then cooled, filtered, and the filter residue is washed with methanol, to give 43 g of a compound of formula

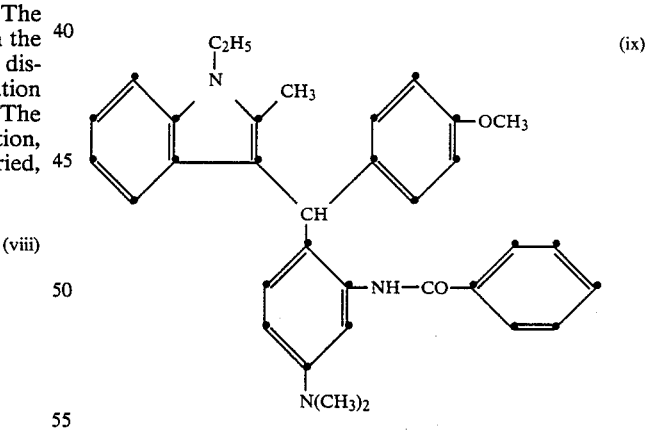

which melts at 178°–178.5° C.

2.5 g of the compound of formula (ix) are dissolved in 25 ml of acetone and 10.4 g of iron(III) chloride hexahydrate are added to the solution. After 20 hours at room temperature, the reaction mixture is concentrated and the residue is dissolved in toluene. After treatment with 80 ml of 10% sodium hydroxide solution, the organic phase is separated, treated with activated carbon, dried over sodium sulfate and concentrated. The residue is chromatographed over silica gel, to give 0.4 g of a benzoxazine of formula

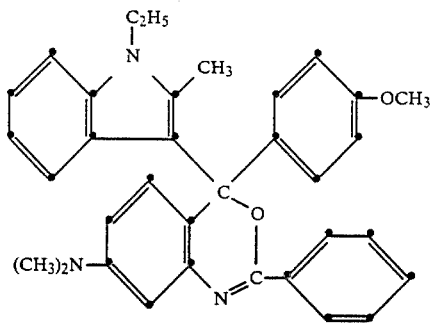

(14)

which melts at 119°–124° C.

This benzoxazine produces a bluish-green image on acid clay.

In the same manner as described in Examples 1 to 4, the following benzoxazines of formula

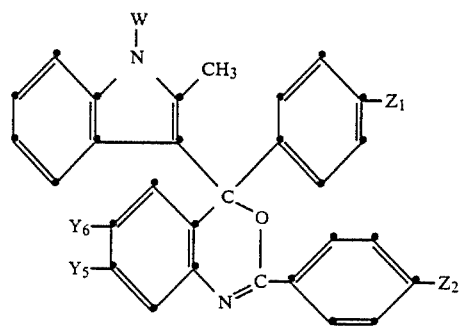

(15)

listed in the Table are obtained using the appropriate starting materials and produce the indicated colour on acid clay.

TABLE

| Ex. | W | $Z_1$ | $Z_2$ | $Y_5$ | $Y_6$ | Color |
|-----|------|------------|------|------------|--------|---------------|
| 5 | —$CH_3$ | —$OC_2H_5$ | H | —$OCH_3$ | H | pink |
| 6 | —$C_2H_5$ | —$OCH_3$ | Cl | —$OCH_3$ | —$OCH_3$ | red |
| 7 | —$C_8H_{17}$ | —$OCH_3$ | H | —$OCH_3$ | $CH_3$ | pink |
| 8 | —$C_2H_5$ | —$N(CH_3)_2$ | Cl | —$N(C_2H_5)_2$ | H | bluish-black |
| 9 | —$C_8H_{17}$ | —$N(C_2H_5)_2$ | H | —$N(CH_3)_2$ | H | bluish-black |
| 10 | —$C_2H_5$ | —$N(CH_3)_2$ | H | —$OCH_3$ | $CH_3$ | greenish-blue |
| 11 | —$C_2H_5$ | pyrrolidino | H | —$N(CH_3)_2$ | H | black |
| 12 | —$C_8H_{17}$ | pyrrolidino | H | —$OCH_3$ | $CH_3$ | greenish-blue |
| 13 | —$C_2H_5$ | N-methyl-anilino | Cl | —$OCH_3$ | $CH_3$ | green |

EXAMPLE 14

Preparation of a pressure-sensitive copying paper

A solution of 3 g of the benzoxazine of formula (11) obtained in Example 1 in 80 g of diisopropylnaphthalene and 17 g of kerosene are microencapsulated by coacervation in a manner known per se with gelatin and gum arabic. The microcapsules are mixed with starch solution and coated on a sheet of paper. The face of a second sheet of paper is coated with activated clay as colour developer. The first sheet containing the colour former and the sheet coated with the developer are laid on top of each other with the coated sides face to face. Pressure is exerted on the first sheet by writing by hand or typewriter and a strong pink copy of excellent fastness to light develops immediately on the sheet coated with the developer.

EXAMPLE 15

1 g of the benzoxazine obtained in Example 1 is dissolved in 17 g of toluene. With stirring, 12 g of polyvinyl acetate, 8 g of calcium carbonate and 2 g of titanium dioxide are added to this solution. The resultant suspension is diluted with toluene in the weight ratio 1:1 and applied to a sheet of paper with a knife to a thickness of 10 μm. On this sheet of paper is laid a second sheet, the underside of which has been coated to a weight of 3 g/m² with a mixture consisting of 1 part of an amide wax, 1 part of a stearin wax and 1 part of zinc chloride. Pressure is exerted on the top sheet by hand or typewriter and a strong and lightfast pink copy develops immediately on the sheet coated with the colour former.

EXAMPLE 16

Preparation of a heat-sensitive recording material

In a ball mill, 32 g of 4,4'-isopropylidenediphenol (bisphenol A), 3.8 g of the distearylamide of ethylenediamine, 39 g of kaolin, 20 g of an 88% hydrolysed polyvinyl alcohol and 500 ml of water are ground to a particle size of about 5 μm. In a second ball mill, 6 g of the benzoxazine obtained in Example 1, 3 g of a 88% hydrolysed polyvinyl alcohol and 60 ml of water are ground to a particle size of about 3 μm. Both dispersions are mixed and applied to paper to a dry coating weight of 5.5 g/m². A strong pink colour of excellent fastness to light and sublimation is produced by contacting the paper with a heated ball-point pen.

What is claimed is:

1. A chromogenic 1-heterocyclic substituted 2,4-benzoxazine of formula

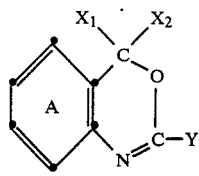   (1)

wherein $X_1$ and $X_2$ are identical or different heteroaromatic radicals selected from the group consisting of pyrrolyl, thienyl, indolyl, benzofuranyl, benzothienyl and naphthothienyl, wherein said radicals are unsubstituted, C-substituted by halogen, hydroxyl, cyano, nitro, lower alkyl, lower alkoxy, lower alkoxycarbonyl, $C_1$–$C_8$-acyl, amino, lower alkylamino, di-lower alkylamino, $C_5$–$C_6$-cycloalkyl, benzyl or phenyl, or N-substituted by $C_1$–$C_{12}$-alkyl, $C_2$–$C_{12}$-alkenyl, $C_1$–$C_8$-acyl, benzyl or phenethyl, each of which is unsubstituted or substituted by cyano, halogen, nitro, hydroxy, lower alkyl, lower alkoxy or lower alkoxycarbonyl, said heteroaromatic radicals being bonded to the oxazine ring through a carbon atom of a heterocyclic ring of said heteroaromatic radical, and $X_2$ is also an aryl radical, Y is hydrogen, alkyl, cycloalkyl, aryl, aralkyl or a heterocyclic radical selected from the group consisting of furyl, thienyl, pyrrolyl, pyrazolyl, imidazolyl and pyridyl, and the benzene ring A is substituted by halogen, cyano, nitro, lower alkyl, lower alkoxy, lower alkylthio, lower alkylcarbonyl, lower alkoxycarbonyl or —$NR_1$—$R_2$, in which $R_1$ and $R_2$ are each independently of the other hydrogen, alkyl of not more than 12 carbon atoms which is unsubstituted or substituted by halogen, hydroxy, cyano or lower alkoxy, or are cycloalkyl of 5 to 10 carbon atoms, or phenalkyl or phenyl, each unsubstituted or ring-substituted by halogen, cyano, lower alkyl or lower alkoxy, or —$NR_1R_2$ is a 5- or 6-membered heterocyclic radical.

2. A benzoxazine according to claim 1, wherein $X_1$ and $X_2$ are each independently of the other a pyrrolyl, thienyl, indolyl, benzofuranyl, benzothienyl or naphthothienyl radical.

3. A benzoxazine according to claim 1, wherein $X_1$ is a 1-$C_1$–$C_8$-alkylpyrrol-(2)-yl or 1-$C_1$–$C_8$-alkyl-2-methyl-indol-(3)-yl radical.

4. A benzoxazine according to claim 1, wherein $X_2$ is a phenyl or naphthyl radical, each unsubstituted or substituted by halogen, cyano, lower alkyl, cycloalkyl, acyl, acylamino, —$NR_3R_4$, —$OR_3$ or —$SR_3$, wherein $R_3$ and $R_4$ are each independently of the other hydrogen, alkyl of not more than 12 carbon atoms which is unsubstituted or substituted by halogen, hydroxy, cyano or lower alkoxyy, or are cycloalkyl of 5 to 10 carbon atoms or phenalkyl or phenyl, each unsubstituted or ring-substituted by halogen, cyano, lower alkyl or lower alkoxy, or —$NR_3R_4$ is a 5- or 6-membered heterocyclic radical.

5. A benzoxazine according to claim 4, wherein $X_2$ is a substituted phenyl radical of formula

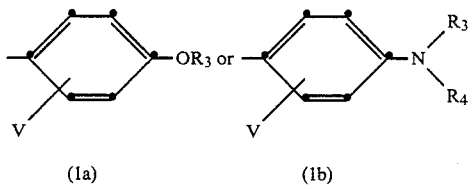

wherein $R_3$ and $R_4$ are each independently of the other hydrogen, alkyl of not more than 12 carbon atoms which is unsubstituted or substituted by halogen, hydroxy, cyano or lower alkoxy, or are cycloalkyl of 5 to 10 carbon atoms or phenalkyl or phenyl, each unsubstituted or ring-substituted by halogen, cyano, lower alkyl or lower alkoxy, or —$NR_3R_4$ is a 5- or 6-membered heterocyclic radical, and V is hydrogen, halogen, lower alkyl, $C_1$–$C_{12}$alkoxy, $C_1$–$C_{12}$acyloxy, benzyl, phenyl, benzyloxy, phenoxy, or benzyl or benzyloxy, each substituted by halogen, cyano, lower alkyl or lower alkoxy, or is the group —$NT_1T_2$, wherein $T_1$ and $T_2$, each independently of the other, are hydrogen, lower alkyl, cycloalkyl, benzyl or benzyl which is substituted by halogen, cyano, lower alkyl or lower alkoxy, or are $C_1$–$C_8$acyl, and $T_1$ is also phenyl or phenyl which is substituted by halogen, cyano, lower alkyl or lower alkoxy.

6. A benzoxazine according to claim 1, wherein Y is phenyl or phenyl which is substituted by halogen, trifluoromethyl, cyano, lower alkyl or lower alkoxy.

7. A benzoxazine according to claim 1, wherein the ring A is a benzene ring which is substituted in meta-position to the nitrogen bond by lower alkoxy or by —$NR_1R_2$.

8. A benzoxazine according to claim 7, wherein the benzene ring is additionally substituted by halogen, lower alkoxy or lower alkyl.

9. A benzoxazine according to claim 1 of formula (2)

wherein B is a substituted phenyl radical of formula (2a)    (2b)

$Y_1$ is lower alkoxy or di-lower alkylamino, $Y_2$ is phenyl or phenyl which is substituted by halogen, trifluoromethyl, lower alkyl or lower alkoxy, $W_1$ is hydrogen, $C_1$–$C_8$alkyl or $C_1$–$C_8$alkyl which is substituted by cyano or lower alkoxy, or is acetyl, propionyl or benzyl, $W_2$ is lower alkyl or phenyl, $R_5$, $R_6$ and $R_7$ are each independently alkyl of not more than 12 carbon atoms which is unsubstituted or substituted by hydroxy, cyano or lower alkoxy, or are $C_5$-$C_6$cycloalkyl, benzyl, phenethyl or phenyl, or —$NR_6R_7$ is pyrrolidino, piperidino or morpholino, $V_1$ is hydrogen, halogen, lower alkyl, $C_1$-$C_8$alkoxy, benzyloxy or the group —$NT_3T_4$, $T_3$ and $T_4$ are each independently of the other hydrogen, lower alkyl, lower alkylcarbonyl or benzoyl or benzoyl which is substituted by halogen, methyl or methoxy, and the rings $A_1$ and D are each independently of the other unsubstituted or substituted by halogen or lower alkyl.

10. A benzoxazine according to claim 9, wherein B is a substituted phenyl radical of formula (2a), $V_1$ is hydrogen, $W_1$ is $C_1$-$C_8$alkyl, $W_2$ is methyl and $Y_1$ is lower alkoxy.

11. A benzoxazine according to claim 1 of formula

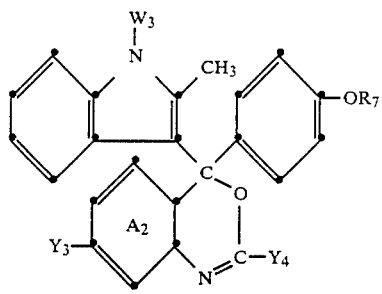

(3)

wherein $A_2$ is unsubstituted or substituted by halogen or methyl, $Y_3$ is lower alkoxy, $R_7$ and $W_3$ are each independently of the other lower alkyl, and $Y_4$ is phenyl, tolyl or chlorophenyl.

12. A benzoxazine according to claim 11, wherein $A_2$ is substituted by methyl, $Y_3$ is methoxy, $W_3$ is ethyl, $R_7$ is methyl and $Y_4$ is phenyl or chlorophenyl.

* * * * *